United States Patent
Brewer et al.

(10) Patent No.: US 6,274,625 B1
(45) Date of Patent: Aug. 14, 2001

(54) ANTI-MICROBIAL COMPOUND

(75) Inventors: Mark Brewer, Chester; Rajeshkumar Patel, Liverpool; Steve Woolley, Flintshire, all of (GB)

(73) Assignee: Associated Octel Company Limited, London (GB)

( * ) Notice: Subject to any disclaimer, the term of this patent is extended or adjusted under 35 U.S.C. 154(b) by 0 days.

(21) Appl. No.: 09/509,805

(22) PCT Filed: Oct. 8, 1998

(86) PCT No.: PCT/GB98/03025
§ 371 Date: Jun. 15, 2000
§ 102(e) Date: Jun. 15, 2000

(87) PCT Pub. No.: WO99/18791
PCT Pub. Date: Apr. 22, 1999

(30) Foreign Application Priority Data

Oct. 9, 1997 (GB) .................................................. 9721394

(51) Int. Cl.[7] ...................................................... A01N 37/12
(52) U.S. Cl. ........................ 514/566; 514/566; 514/836; 424/409; 424/405; 604/290; 604/294
(58) Field of Search .................................... 514/566, 836, 514/912; 604/290, 294; 424/405, 409, 423, 604, 618, 630

(56) References Cited

FOREIGN PATENT DOCUMENTS

0717102 A1 * 6/1996 (EP) ................................ C11D/3/39

* cited by examiner

Primary Examiner—Karen Cochrane Carlson
Assistant Examiner—Patricia Robinson
(74) Attorney, Agent, or Firm—Fay, Sharpe, Fagan, Minnich & McKee, LLP

(57) ABSTRACT

There is provided use of an amino acid derivative in free acid or salt form, in which the nitrogen atoms of two or more amino acid molecules are linked by a hydrocarbyl or substituted hydrocarbyl group, as an anti-fungal compound.

22 Claims, 14 Drawing Sheets

Figure 11:
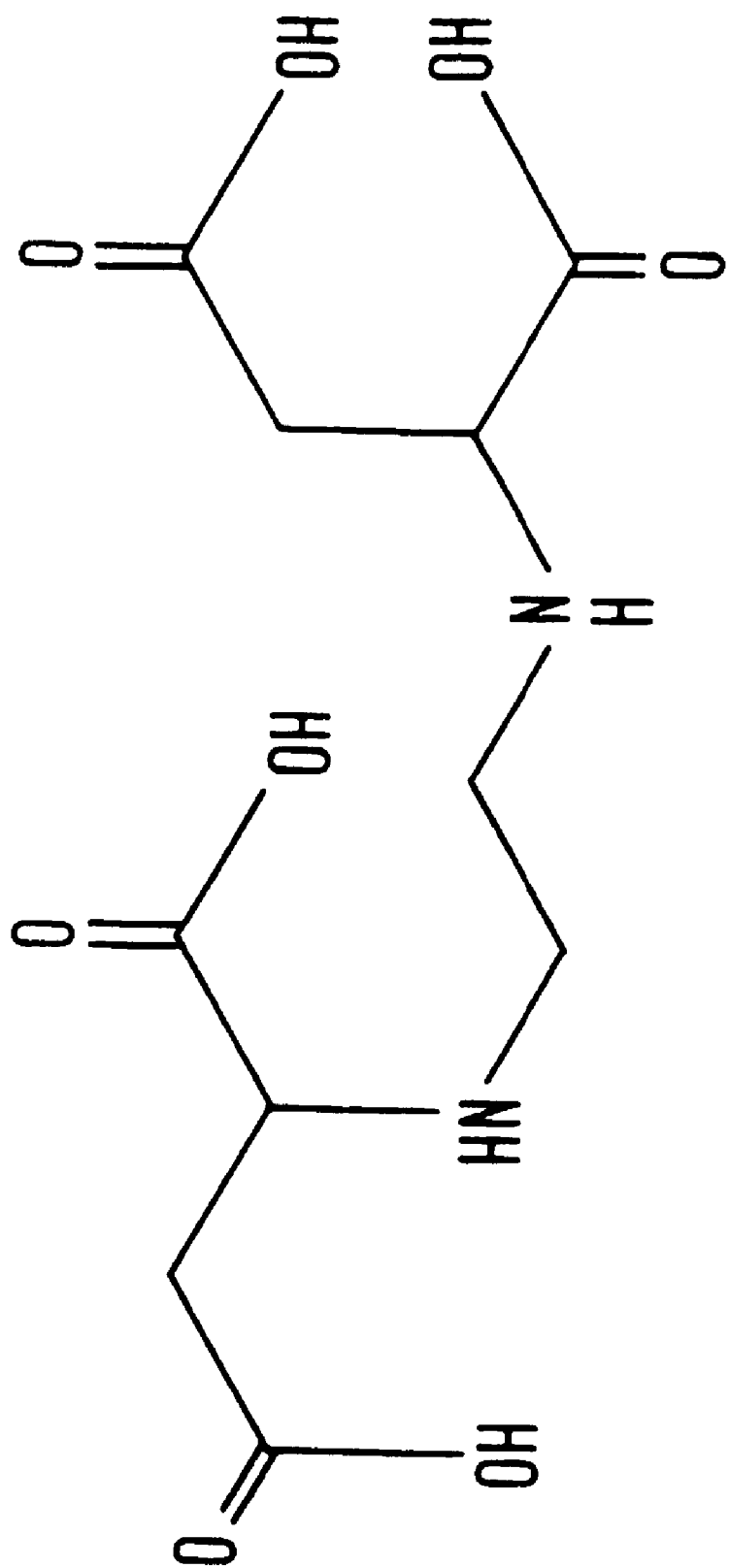

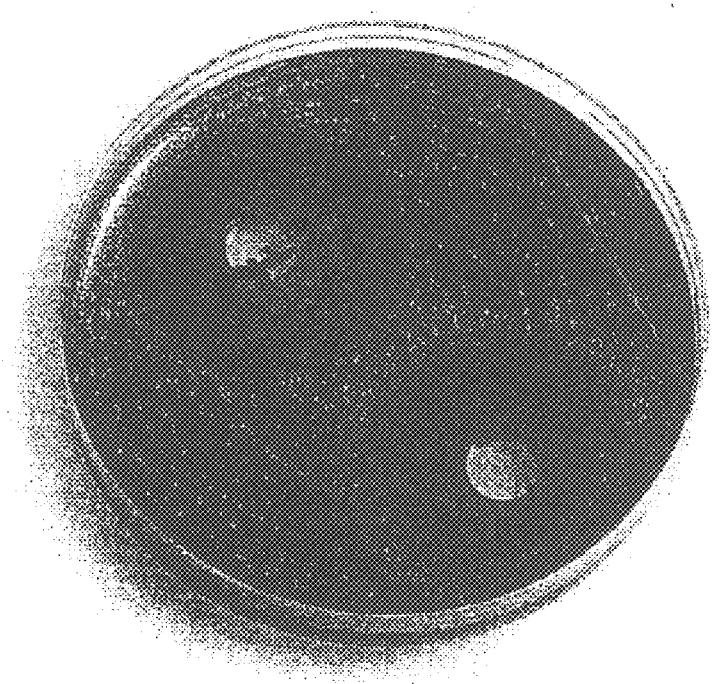
FIG. 1  Inhibition of Esch. coli by EDDS
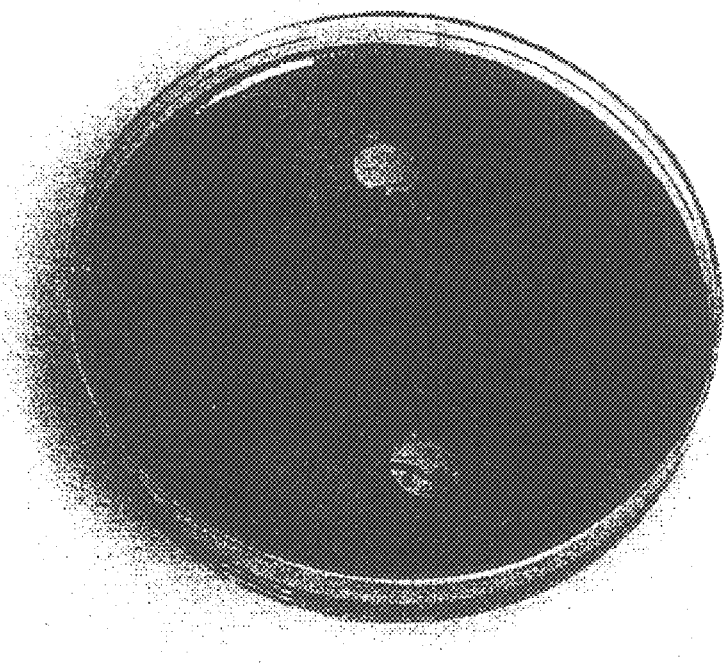
FIG. 2  Inhibition of Pseudomonas sp by EDDS

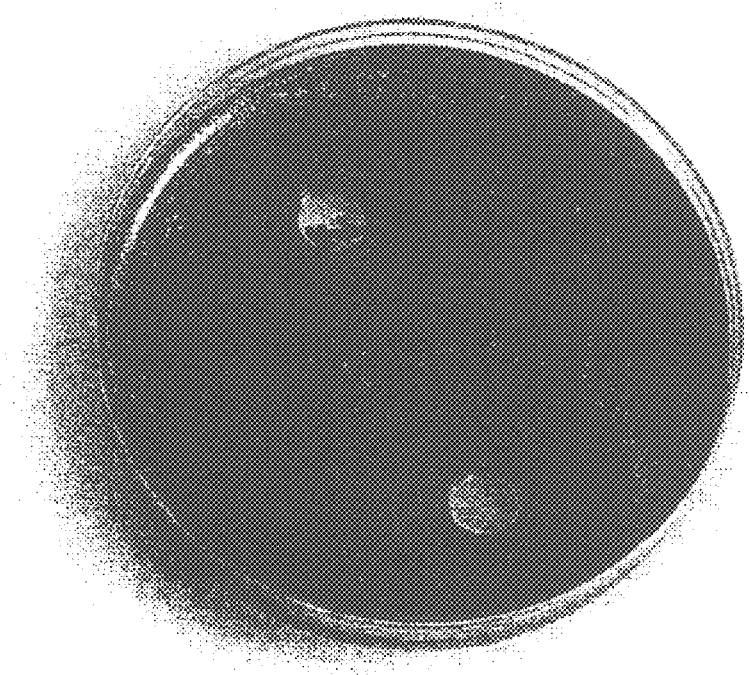
FIG. 3  Inhibition of Staphylococcus aureus by EDDS
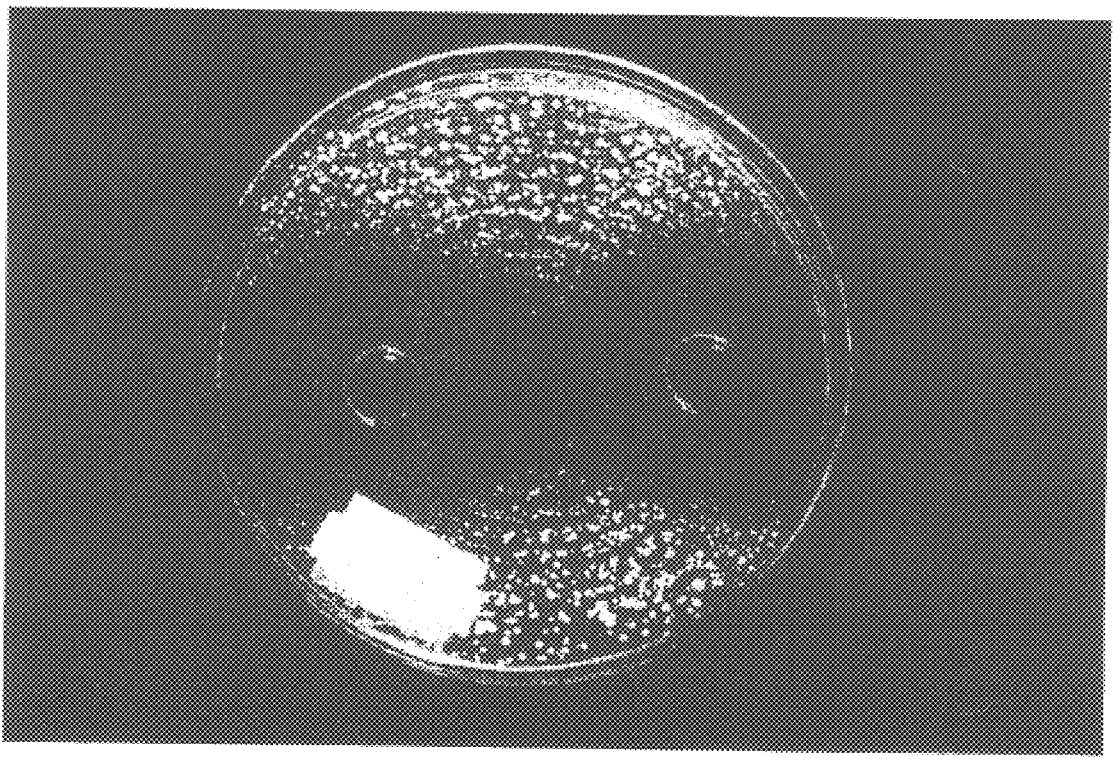
FIG. 4  Inhibition of Candida albicans by EDDS

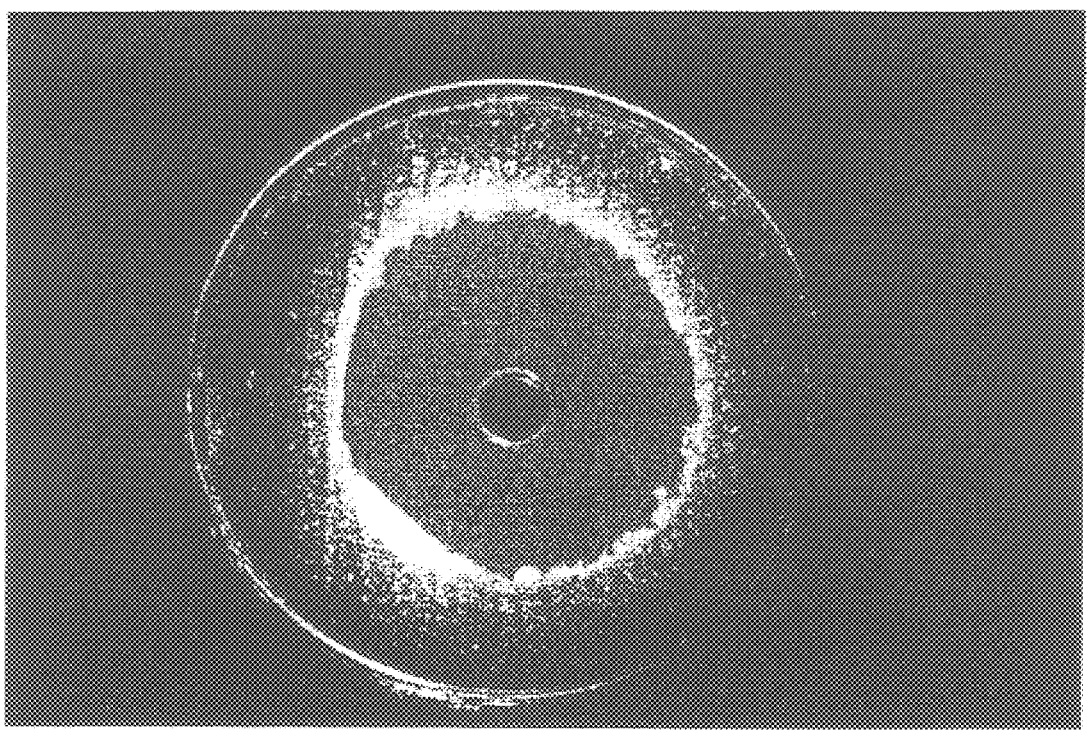
FIG. 5  Inhibition of Aspergillus Niger by EDDS
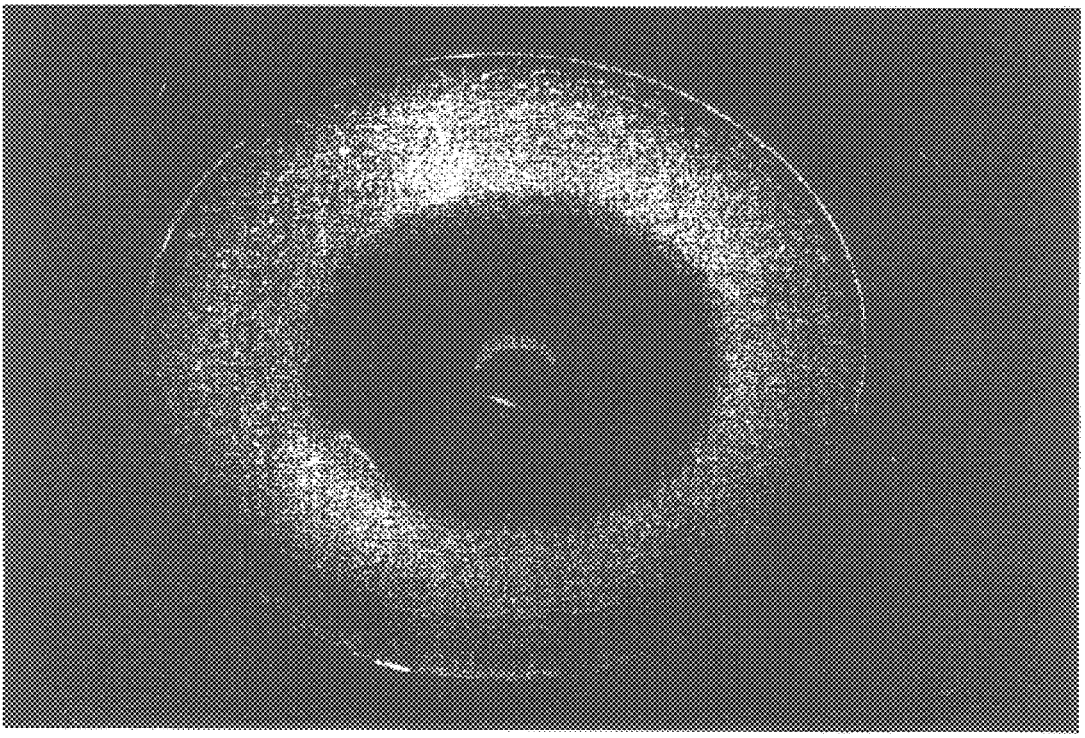
FIG. 6  Inhibition of Mucor sp by EDDS

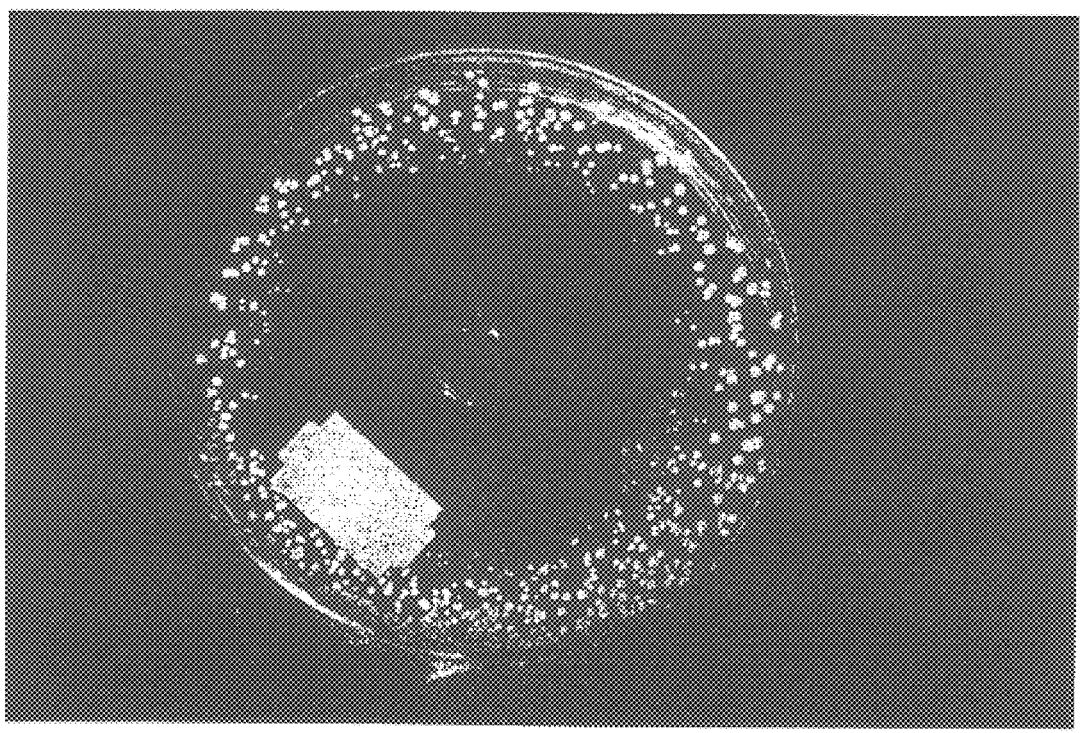
FIG. 7  Inhibition of Candida pseudotropicalis by EDDS
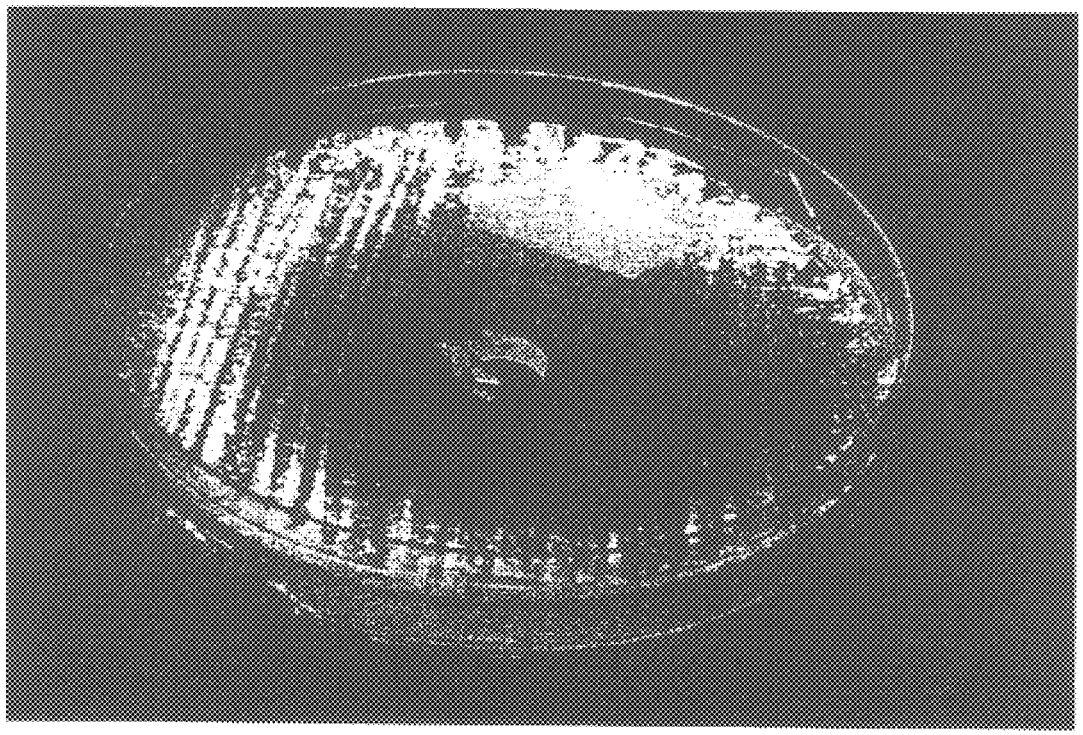
FIG. 8  Partial Inhibition of Penicillium sp by EDDS

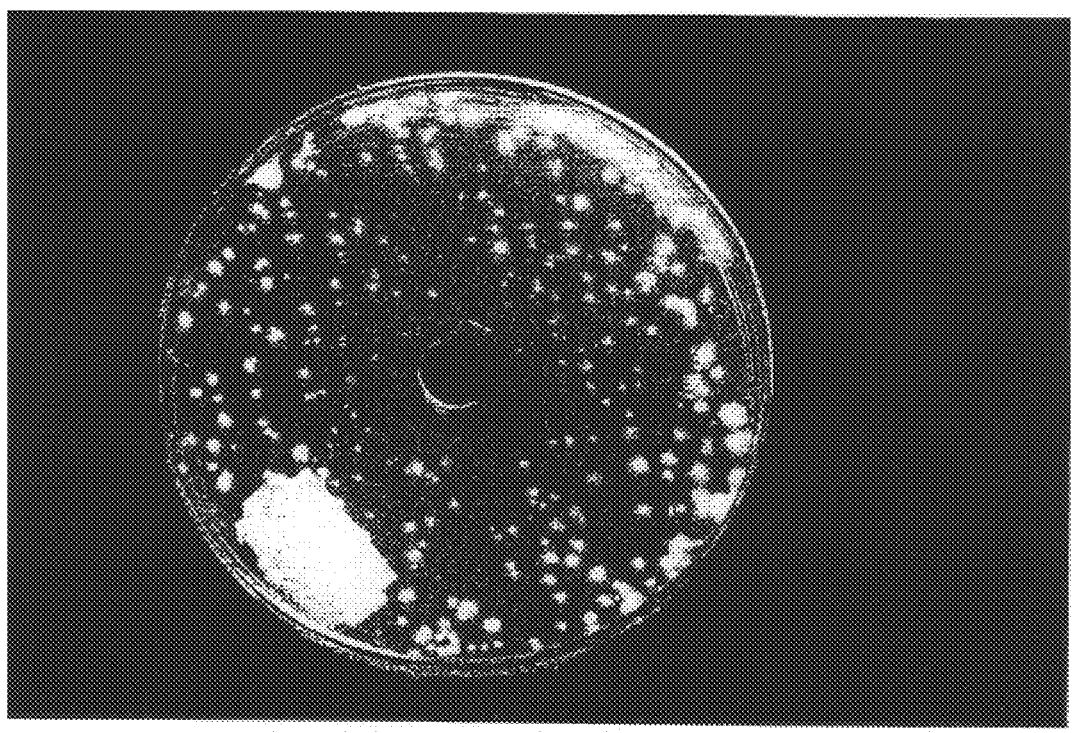
FIG. 9 Partial Inhibition of Fusarium sp by EDDS
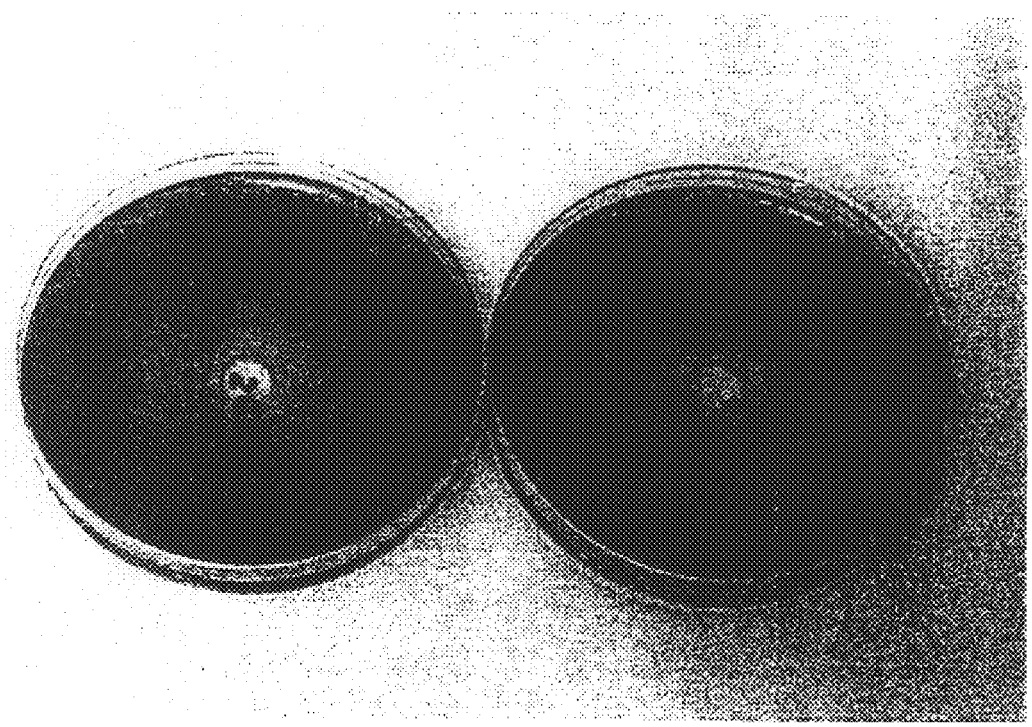
FIG. 10 Inhibition of contaminant Aeromonas sp by EDDS

ANTI-MICROBIAL COMPOUND

This invention relates to the use of an amino acid derivative as an anti-fungal and/or anti-bacterial compound.

Compounds having anti-microbial activity are desirable in many applications to prevent the growth of microbe contaminants. Anti-microbial activity includes anti-bacterial activity and anti-fungal activity.

Bacteria and fungi are prevalent in the environment. It has been known for very many years that compounds may be active against either bacteria or fungi. This activity is as a result of one of many mechanisms. A few compounds have been isolated which are active against both bacteria and fungi.

Anti-microbial compounds have uses in many applications.

The presence of bacteria and/or fungi may, for example, result in spoilage of food products including agricultural food products such as micronutrients, may contaminate water, either rendering drinking water unfit for consumption or allowing microbial growth in apparatus through which water may be introduced. Furthermore, the presence of bacteria and/or fungi on the fabrics or the body is not desirable and the bacteria and/or fungi may be removed with detergents compositions or personal care products.

WO 97/02010 teaches a number of chelants which may act as anti-bacterial compounds. These chelants are derivatives of succinic acid, glutaric acid and phosphonic acid. WO 97/02010 only teaches that these compounds are anti-bacterial. No indication is given as to whether these compounds have any other anti-microbial, for example anti-fungal, activity.

The present invention aims to provide a compound or a composition having anti-fungal activity or anti-fungal and anti-bacterial activity. Moreover, in a further aspect, the present invention aims to provide a compound or a composition having anti-bacterial activity and preferably improved anti-bacterial activity.

The present invention provides use of an amino acid derivative in free acid or salt form, in which the nitrogen atoms of two or more amino acid molecules are linked by a hydrocarbyl or substituted hydrocarbyl group, as an anti-fungal compound.

The present invention further provides use of an amino acid derivative in free acid or salt form, in which the nitrogen atoms of two or more amino acid molecules are linked by a hydrocarbyl or substituted hydrocarbyl group, as an anti-fungal and anti-bacterial compound.

In a further aspect, the present invention provides use of an amino acid derivative in free acid or salt form, in which the nitrogen atoms of two or more amino acid molecules are linked by a hydrocarbyl or substituted hydrocarbyl group, as an anti-bacterial compound, with proviso that the amino acid derivative is other than a chelant selected from derivatives of succinic acid, glutaric acid and phosphonic acid.

In yet a further embodiment, the present invention provides use of an amino acid derivative in free acid or salt form, in which the nitrogen atoms of two or more amino acid molecules are linked by a hydrocarbyl or substituted hydrocarbyl group, and in which the amino acid derivative is optically active, as an anti-bacterial compound.

The present invention also covers anti-fungal and/or anti-fungal and anti-bacterial compositions comprising the compounds of the present invention including processes for making the same and uses of the same.

The present invention is advantageous as it overcomes the aforementioned problems associated with the prior art.

In the present specification, unless otherwise indicated, the term anti-microbial means having a microbiostatic effect ie. preventing further microbial growth and/or means having a microbicidal effect ie. killing microbes already present.

In the present specification, unless otherwise indicated, the term anti-bacterial means having a bacteriostatic effect ie. preventing further bacterial growth and/or means having a bactericidal effect ie. killing bacteria already present.

In the present specification, unless otherwise indicated, the term anti-fungal means having a fungistatic effect ie. preventing further fungal growth and/or means having a fungicidal effect ie. killing fungi already present.

In the present specification the term microbe is given its usual meaning, for example as defined in *The Penguin Dictionary of Biology, Eighth Edition* (1992). The term microbe includes bacteria, fungi and yeasts.

In the present specification the term bacteria is given its usual meaning, for example as defined in *The Penguin Dictionary of Biology, Eighth Edition* (1992).

In the present specification the term fungi is given its usual meaning, for example as defined in *The Penguin Dictionary of Biology, Eighth Edition* (1992). The term fungi includes yeasts.

Preferably, the compound used in accordance with the present invention has at least one chiral centre.

Preferably, the compound used in accordance without the present invention has at least two chiral centres.

Preferably, the compound used in accordance with the present invention has at least one (S) chiral centre.

Preferably, the compound used in accordance with the present invention has at least two (S) chiral centres.

Preferably, the compound used in accordance with the present invention is optically active.

The compound used in accordance with the present invention may be a derivative of any one or more of the 26 or so naturally occurring amino acids listed in standard textbooks. Preferably, the amino acid or derivative thereof is a naturally occurring amino acid or derivative thereof.

The amino acid derivative may be any one or more of a "neutral" amino acid, a "basic" amino acid or an "acidic" amino acid.

Examples derivatives of neutral amino acids that may be used in the present invention include derivatives of glycine, alanine, valine, leucine, norleucine, phenylalanine, tyrosine, serine, cystine, threonine, methionine, di-iodotyrosine, thyroxine, dibromotyrosine, tryptophan, proline and hydroxyproline.

Examples derivatives of basic amino acids that may be used in the present invention include derivatives of ornithine, arginine, lysine and histidine.

Examples of derivatives of acidic amino acids that may be used in the process of the present invention include derivatives of aspartic acid, glutamic acid and b-hydroxyglutamic acid.

The preferred derivatives of amino acids for the process of the present invention are derivatives of those with two carboxyl groups and one amino group—i.e. the acidic amino acids listed above. Aspartic acid and glutamic acid are the most preferred of the three.

Specific optical isomers, particularly the L-form, are desirable.

Preferably the compound is selected from the group consisting of L-aspartic acid, L-glutamic acid or L-phenylalanine, including derivatives thereof.

In an alternative embodiment, the present invention relates to the uses or compositions described herein, wherein the amino acid derivative is partially or completely substituted by a second amino acid or derivative thereof, said amino acid or derivative thereof being an acid compound (or salt thereof) comprising at least two nitrogen groups and at least one carboxylic acid group (or salt thereof).

Preferably, the second amino acid is an amino acid derivative as described herein.

Preferably, the compound used in accordance with the present invention comprises at least one succinate group.

Preferably, the compound used in accordance with the present invention comprises at least one ethylene bridge linking two or more amino acids.

Preferably, the compound used in accordance with the present invention is ethylenediamine disuccinic acid (EDDS).

Preferably, the compound used in accordance with the present invention is (S,S) ethylenediamine disuccinic acid [(S,S) EDDS].

The term "EDDS" includes racemic EDDS or optically active isomers thereof, such as (S,S)EDDS, and active salts and active derivatives thereof. Preferably the term means (S,S)EDDS or salts thereof. Preferably the EDDS is (S,S) EDDS.

The finding by the applicant that EDDS, derivatives thereof and in particular (S,S) EDDS act as described above, namely as an anti-fungal and/or anti-bacterial agent, is particularly surprising. It is known that EDDS and (S,S) EDDS are biodegradable. A person skilled in this art would expect that EDDS would degrade on contact with microbial material such as bacteria or fungi. As a consequence of this teaching from the art, it is extremely surprising that EDDS is active as an anti-bacterial and anti-fungal agent and that (S,S) EDDS in particular is active as an anti-bacterial or an anti-fungal agent.

In an alternative embodiment, the present invention relates to the use of an amino acid derivative as described above as an anti-fungal compound, wherein the compound is effective against fungi other than Paecilomyc es Lilacinus, Exophialia sp., and Beauveria sp.

Preferably the compounds for use in accordance with the present invention is in the salt form. Preferably, the amino acid derivative is in its sodium salt form.

In a further embodiment the present invention provides an anti-fungal composition having as its active agent at least an amino acid derivative in free acid or salt form, in which the nitrogen atoms of two or more amino acid molecules are linked by a hydrocarbyl or substituted hydrocarbyl group.

In yet a further embodiment the present invention provides a anti-fungal and anti-bacterial composition having as its active agent at least an amino acid derivative in free acid or salt form, in which the nitrogen atoms of two or more am ino acid molecule s are inhed by a hydrocarbyl or substituted hydrocarbyl group.

In a further embodiment the present invention provides a composition having just anti-bacterial activity having as its active agent at least an amino acid derivative in free acid or salt form, in which the nitrogen atoms of two or more amino acid molecules are linked by a hydrocarbyl or substituted hydrocarbyl group, as an anti-bacterial compound, with proviso that the amino acid derivative is other than a chelant selected from derivatives of succinic acid, glutaric acid and phosphonic acid.

In a further embodiment the present invention provides an anti-bacterial composition having as its active agent at least an amino acid derivative in free acid or salt form, in which the nitrogen atoms of two or more amino acid molecules are linked by a hydrocarbyl or substituted hydrocarbyl group, and in which the amino acid derivative is optically active.

The composition for use in accordance with the present invention may comprise less than 50% w/w amino acid derivative, from 50 to 20% w/w, from 40 to 25 or from 40 to 30% w/w. The composition may comprise less than 20% w/w, less than 10% w/w, less than 1% w/w, less than 0.05% w/w or between 0.05% and 0.01% w/w.

The composition for use in accordance with the present invention may have a pH of from 2 to 14 or from 5 to 12; the compositions may have a pH of from 8 to 10, or from 8.5 to 9.5, or approximately 9. Alternatively, the composition may have a pH of 2 to 4, 4 to 6, 6 to 12, 12 to 14.

In a preferred embodiment, the composition for use in accordance with the present invention is in the form of a solution. Preferably, the solution is an aqueous solution.

Anti-microbial including anti-bacterial and/or anti-fungal compounds or compositions have a large number of uses. Examples of applications in which they may be utilizd are personal care, industrial, institutional or household cleaning, in particular for sanitary cleaning, metal treatment including metal cleaning, water treatment, electroless plating, agriculture and food production including dairy cleaning and brewery cleaning, oil extraction and oil production.

In a further aspect of the present invention, there is provided the use of an amino acid derivative in free acid or salt form, in which the nitrogen atoms of two or more amino acid molecules are linked by a hydrocarbyl or substituted hydrocarbyl group, in a composition comprising at least one anti-fungal compound to increase the activity of the at least one anti-fungal compound.

The applicants have surprisingly found by combining the compound used in accordance with the present invention with a further anti-fungal compound, the anti-fungal activity of the other anti-fungal compound is increased.

The compounds for use in accordance with the present invention may be produced by any known technique. Typically, EDDS may be prepared by the process of GB 9607694.8, PCT/GB96/00894 or PCT/GB94/02397.

Preferably the EDDS is (S,S)EDDS as prepared by the process of PCT/GB94/02397 filed Nov. 2, 1994. In short, PCT/GB94/02397 discloses a process for the preparation of amino acid derivatives in free acid or salt form, in which the nitrogen atoms of two or more amino acid molecules are linked by a hydrocarbonyl or substituted hydrocarbonyl group, which comprises reacting, in an aqueous medium at a pH in the range 7–14, a compound of the formula X—A—Y where X and Y are halo atoms which may be the same or different and A is a hydrocarbonyl or substituted hydrocarbonyl group, in which X and Y are attached to aliphatic or cycloaliphatic carbon atoms, with an amino acid (or salt thereof), wherein the reaction is carried out in the presence of dissolved cations of an alkaline earth metal or of a transition metal.

In a further embodiment PCT/GB94/02397 discloses a process for the preparation of the amino acid derivative, in which the nitrogen atoms of two or more amino acid molecules are linked by a hydrocarbyl or substituted hydrocarbyl group, comprises reacting, in an aqueous medium at a pH in the range 7–14, a compound of the formula X—A—Y where X and Y are halo atoms which may be the same or different and A is a hydrocarbyl or substituted hydrocarbyl group, in which X and Y are attached to aliphatic or cycloaliphatic carbon atoms, with an amino acid (or salt thereof), including the step of recovering unreacted amino acid and recycling it to the process.

Figure 12:
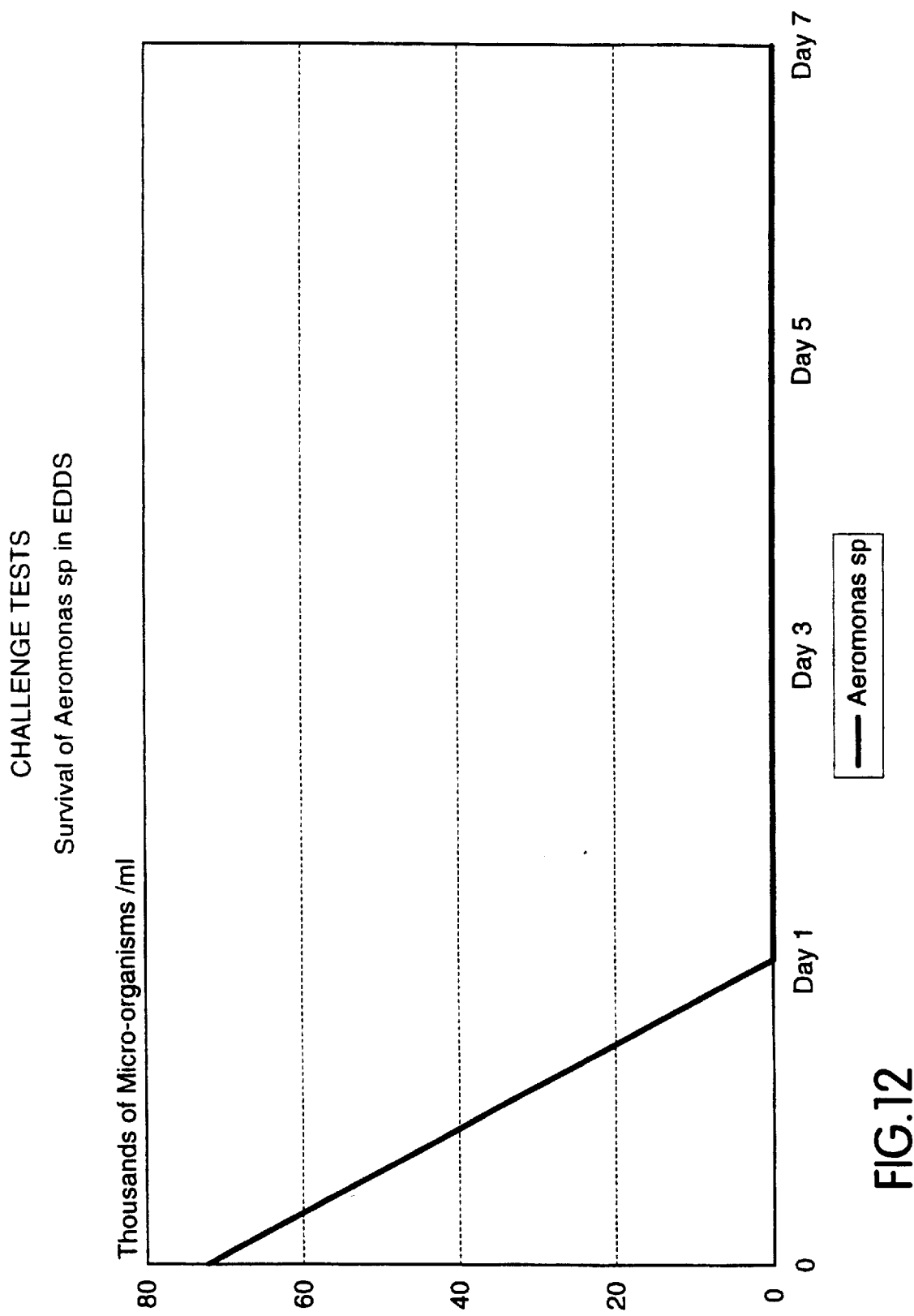
Figure 13:
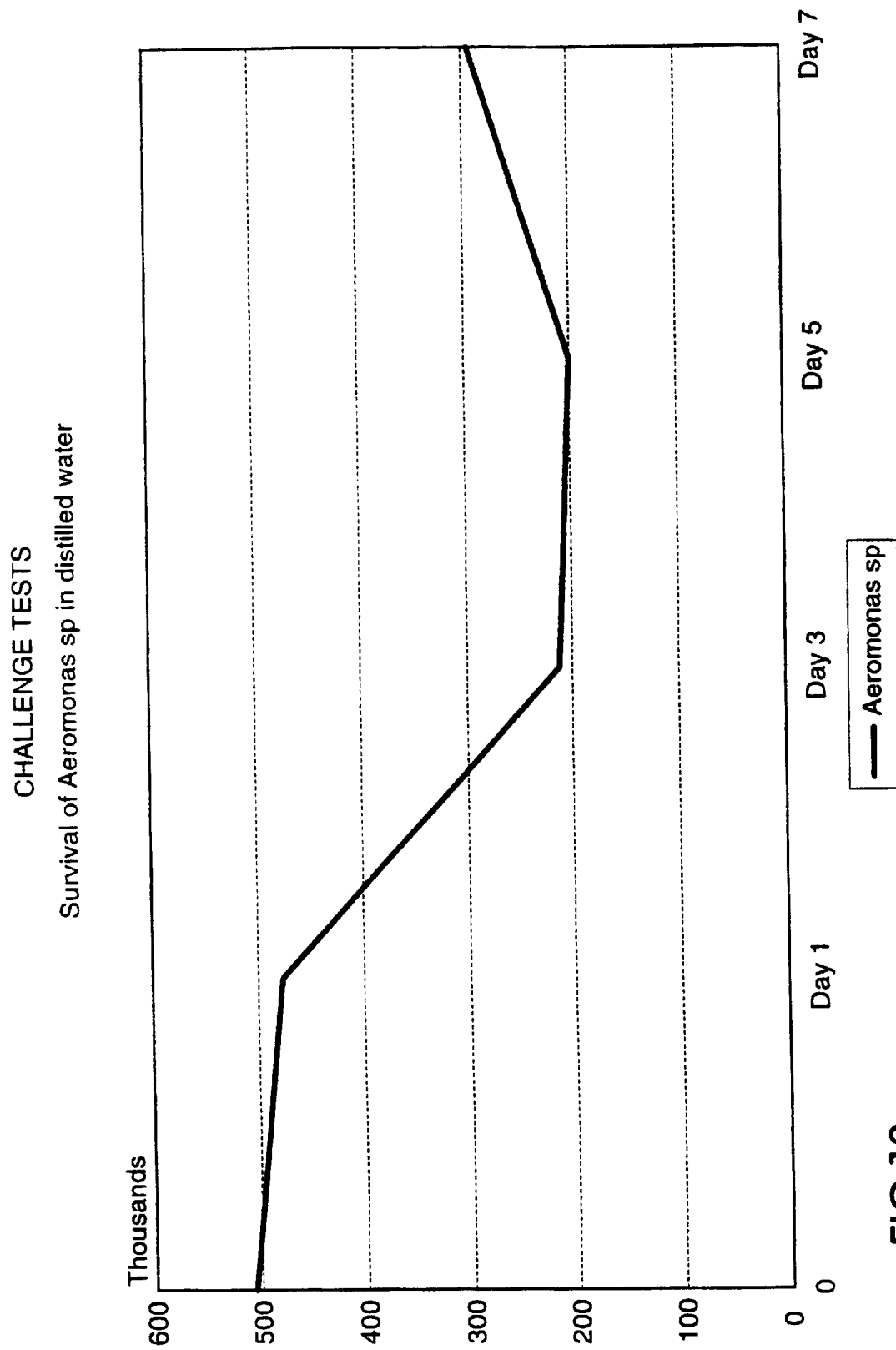
Figure 14:
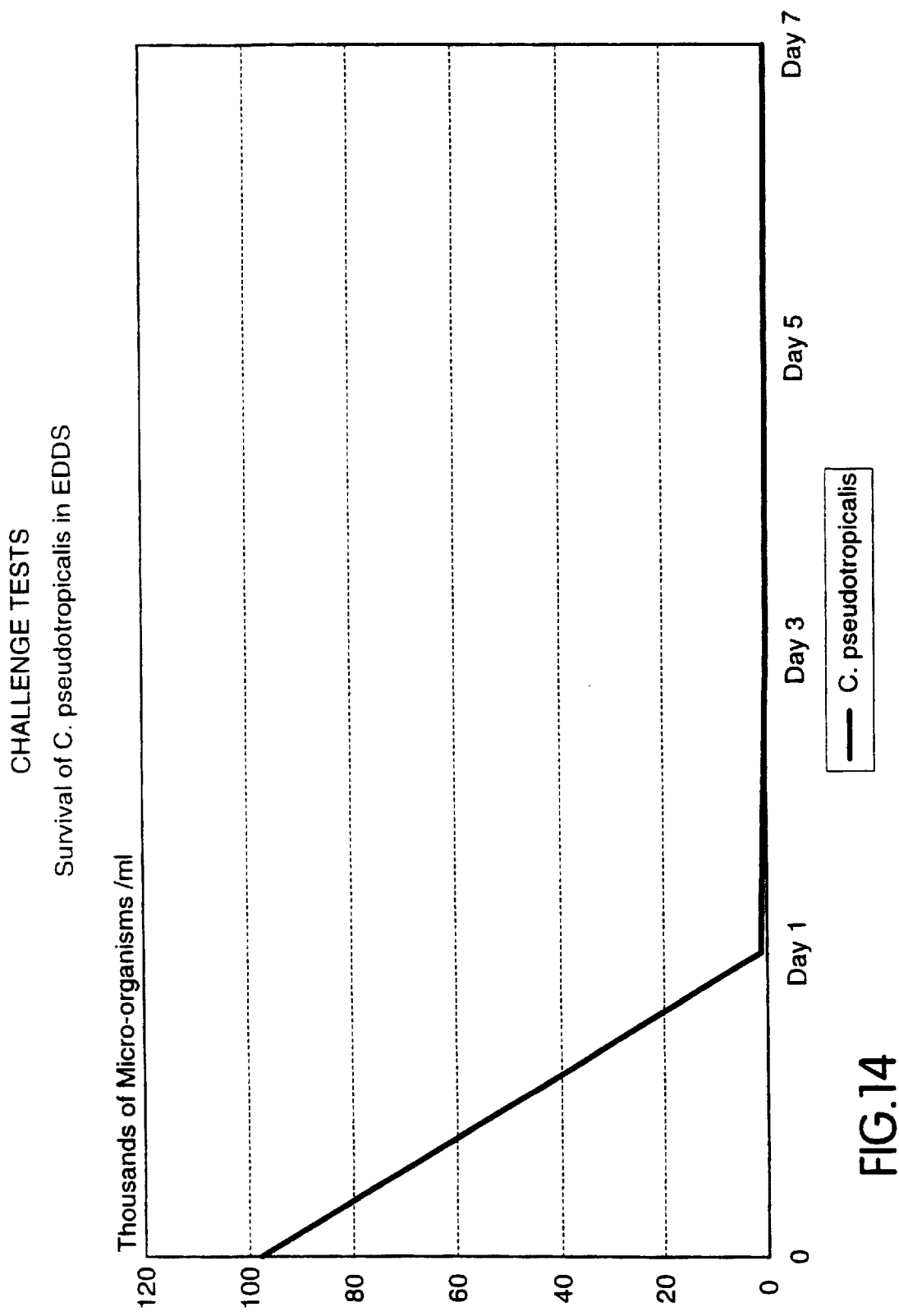
Figure 15:
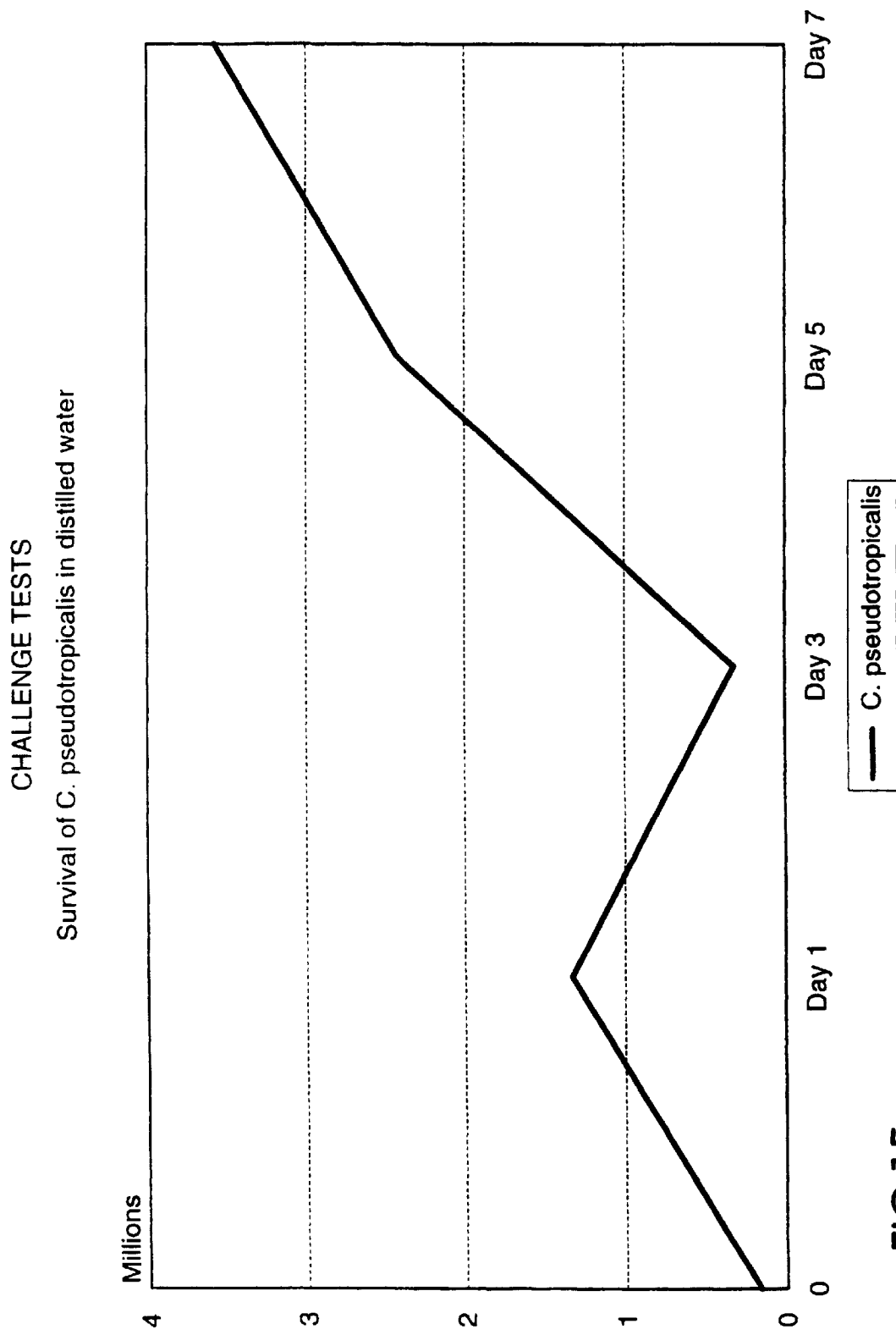
Figure 16:
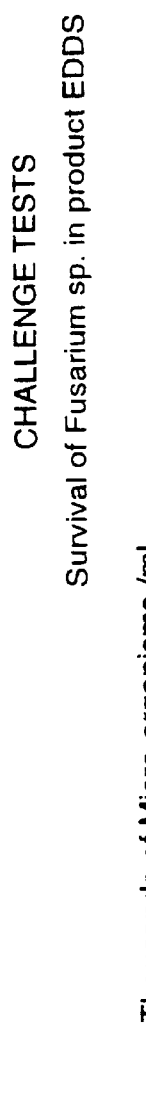
Figure 17:
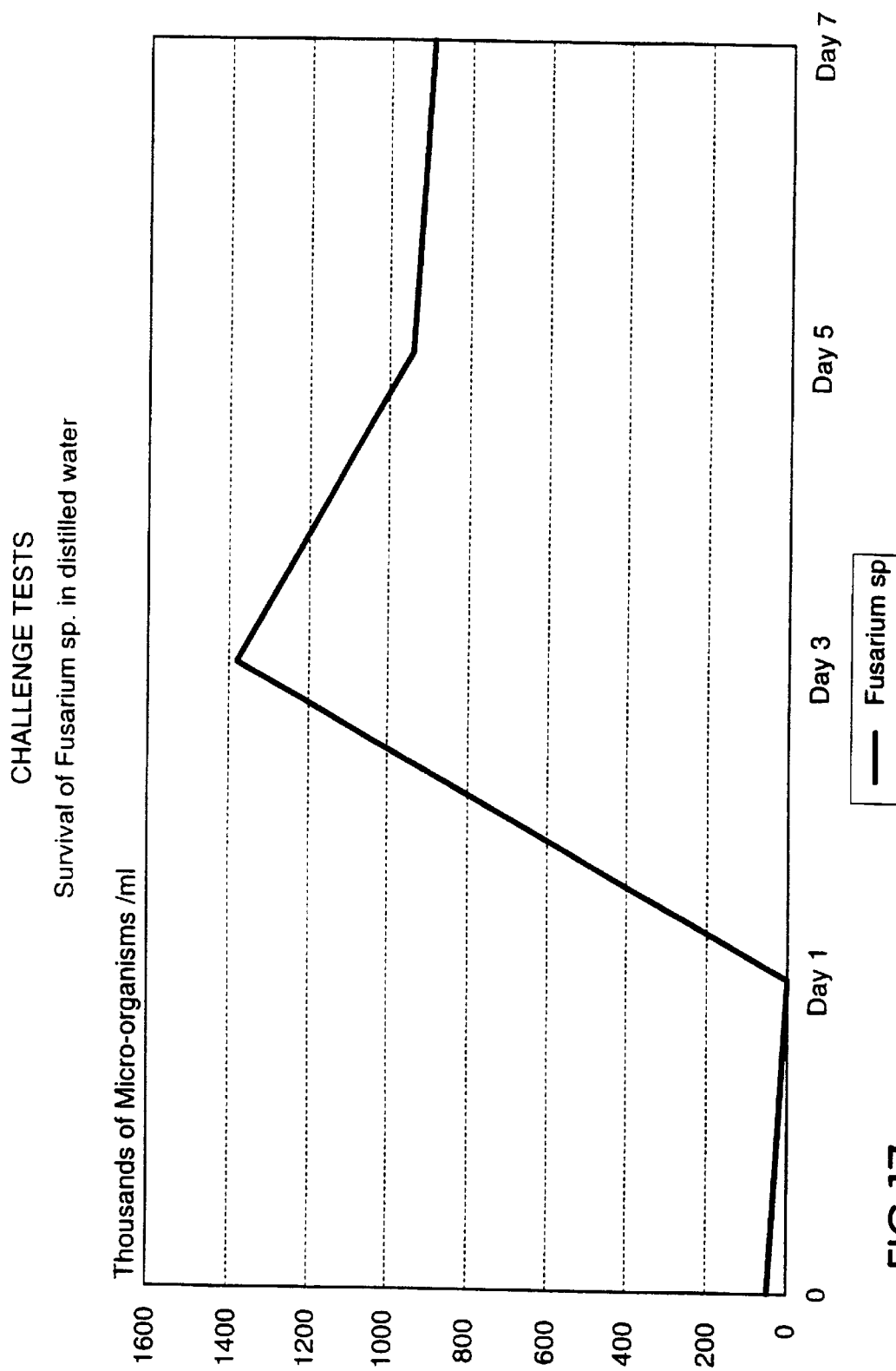
Figure 18:
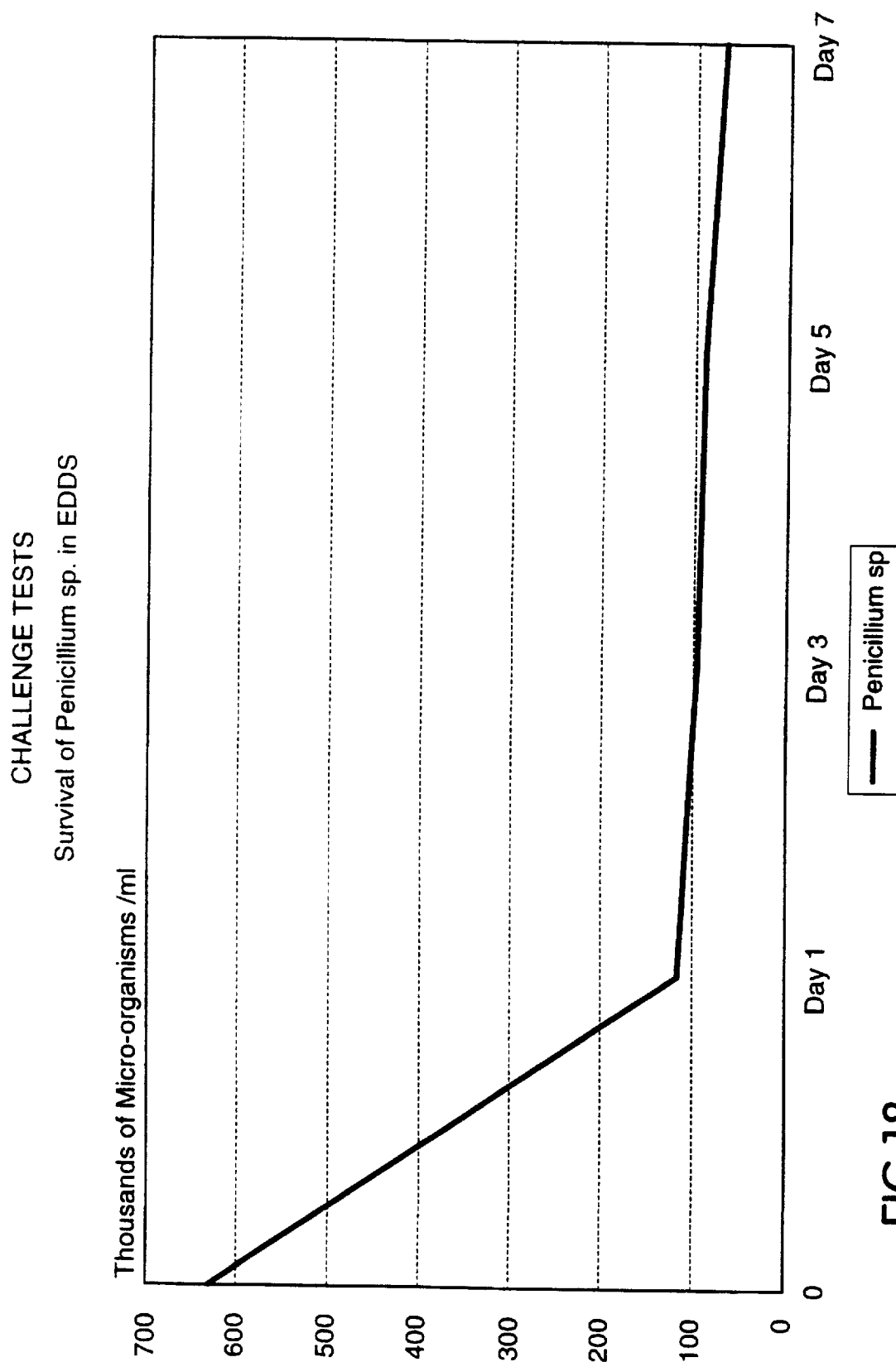
Figure 19:
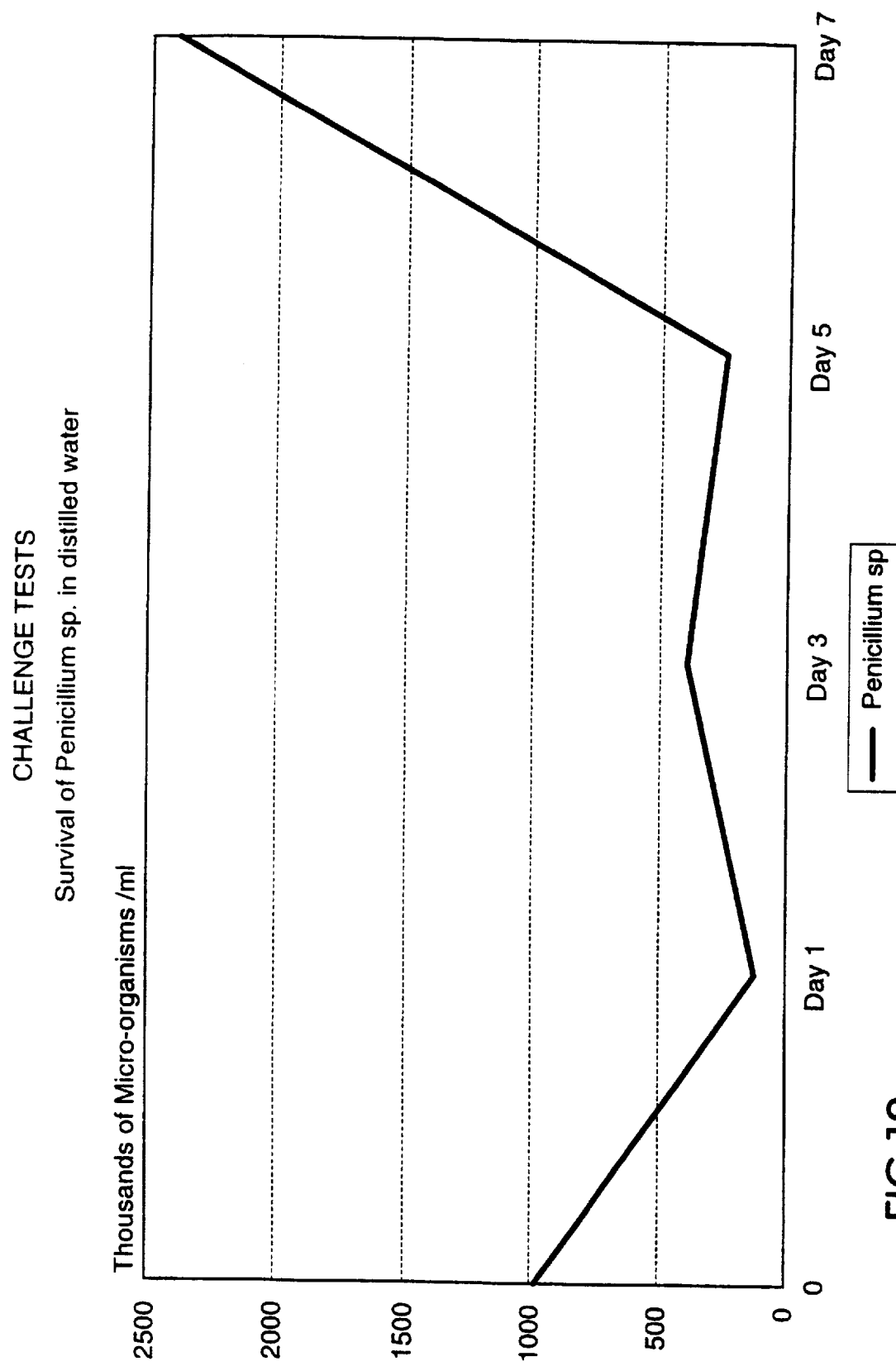

The present invention will now be described, by way of example only, with reference to the accompanied drawings in which:

FIG. 1 is an illustration of an agar test plate;
FIG. 2 is an illustration of an agar test plate;
FIG. 3 is an illustration of an agar test plate;
FIG. 4 is an illustration of an agar test plate;
FIG. 5 is an illustration of an agar test plate;
FIG. 6 is an illustration of an agar test plate;
FIG. 7 is an illustration of an agar test plate;
FIG. 8 is an illustration of an agar test plate;
FIG. 9 is an illustration of an agar test plate;
FIG. 10 is an illustration of an agar test plate;
FIG. 11 is the structure of EDDS;
FIG. 12 is a graph;
FIG. 13 is a graph;
FIG. 14 is a graph;
FIG. 15 is a graph;
FIG. 16 is a graph;
FIG. 17 is a graph;
FIG. 18 is a graph;
FIG. 19 is a graph;

EEDS

The structure of EDDS is shown in FIG. 11.

Preparation of Edds

A preferred method for making EDDS is disclosed in co-pending PCT patent application No. PCT/GB94/02397 filed Nov. 2, 1994. These methods are described above.

For example, (S,S)EDDS may be prepared according to the following teachings, in which DBE means 1,2-dibromoethane.

A reaction mixture containing 150.1 g L-aspartic acid, 140.0 g of 50% aq. NaOH, and 210.9 g water at a pH of 10.2 at 25° C. together with 57.8 g of DBE was heated at 85° C. for 4 hours. During this time an additional 50.1 g of 50% aq. NaOH was added to maintain the pH. At the end of the reaction period the solution was heated to boiling point for 1 hour then cooled to room temperature and 1633 g of water added. The solution was acidified with 36% HCl to pH 3 maintaining the temperature below 50° C. The solid product was collected by filtration. The solid product was (S,S) EDDS (51.5 g on 100% basis), representing a yield on L-aspartic acid charged of 31.3%, no other isomers being detected in the product. In the mother liquors was 85.7 g unreacted L-aspartic acid. The conversion of L-aspartic acid was 42.9% and selectivity to (S,S)EDDS was 72.8%.

ANTI-MICROBIAL STUDIES

Introduction

The anti-microbial properties of product EDDS were assessed using the agar diffusion technique.

Materials and Method

Direct Sensitivity Test agar plates were inoculated over their entire surface with the bacteria listed in table 2. Yeast and fungi (table 2) were inoculated onto Yeast Morphology Agar. Inocula were prepared to a concentration that would produce a confluent growth after incubation.

Plugs of agar 1 cm in diameter were removed from the agar plates and the resultant wells filled with EDDS collected from storage vessels. These storage vessels contained EDDS produced in accordance with the method described above.

Agar plates inoculated with bacterial were incubated at 37° C. for 24 hrs. Aeromonas sp isolated from the product collected from the storage vessels), was also used as a test organism in the agar diffusion assay.

Agar plates inoculated with yeast or fungi were incubated for 72hrs at 30° C.

Intrinsic anti-microbial activity would be apparent by the presence of zones of inhibition forming around the product filled agar wells.

Table 2

TEST ORGANISMS

Bacteria
   *Eschericia coli*
   *Oseudomonas aeruginosa*
   *Staphylococcus aureus*
Yeast and Fungi
   *Aspergillus niger*
   *Candida albicans*
   *Candida pseudotropicalis*
   Gusarium sp
   Mucor sp
   Penicillium sp Results EDDS collected from both storage vessels, produced zones of inhibition to varying degrees against all bacteria, all yeast, all fingi (see table 3 and FIGS. 1 to 9).

The susceptible fungi produced the largest zones of inhibition.

The Aeromonas bacterium produced two concentric zones of inhibition in the diffusion assay, the outer measuring 38 mm in diameter and the inner measuring 24 mm diameter (FIG. 10). This confirms the contaminants susceptibility to the antibacterial properties of the product.

TABLE 3

| DIAMETER OF ZONES OF INHIBITION | |
|---|---|
| Bacteria | |
| *Eschericia coli* | 37 mm |
| *Oseudomonas aeruginosa* | 22 mm |
| *Staphylococcus aureus* | 21 mm |
| Yeast and Fungi | |
| *Aspergillus niger* | 48 mm |
| *Candida albicans* | 45 mm |
| *Candida pseudotropicalis* | 56 mm |
| Fusarium sp | 0 mm |
| Mucor sp | 45 mm |
| Penicillium sp | 0 mm |

Discussion

Anti-bacterial and anti-fungal/yeast activity was exhibited by the product EDDS, as detected by agar diffusion assays, with most organisms displaying large zones of inhibition.

The fungi Fusarium sp. and Penicillium sp., were the only organisms to display a partial resistance to the product. Both fungi produced smaller colonies when in close proximity to the higher concentrations of the product, i.e. closer to the agar well.

The inhibitory activity of the product was effective against bacteria, fungi and yeast.

ACTIVITY OF EDDS IN CHALLENGE TESTS

Materials and Method 10 ml aliquots of product EDDS were transferred to sterile containers, and each container was inoculated with a prepared suspension of one of the organisms listed in Table 4. Similar volumes of sterile distilled waster were also inoculated with these organisms and represented non-inhibitory controls.

Test and control samples were incubated at 30° C. On days 1, 3, 5 and 7, 100μl aliquots were removed from each container and used to prepare a series of ten fold dilutions. 100μl of each dilution was inoculated onto blood agar plates (Aeromonas sp) or Saborauds media (fungi/yeast). After incubation at appropriate temperatures the number of colony forming units in each dilution was noted, and the concentration of bacteria, yeast or fungi in each original inoculum was calculated.

Table 4

ORGANISMS EMPLOYED IN CHALLENGE TESTS

Aeromonas spp

Candida pseudotropicalis

Fusarium spp

Penicillium spp

Results

See FIGS. 12 to 19 and table 5.

TABLE 5

SURVIVAL OF MICROORGANISMS IN EDDS AND DISTILLED WATER
Colony Forming Units per ml

| Organism | | Day 0 | Day 1 | Day 3 | Day 5 | Day 7 |
|---|---|---|---|---|---|---|
| Aeromonas sp. | Dist.water | $5.1 \pm 10^5$ | $4.8 \times 10^5$ | $2.2 \times 10^5$ | $2.0 \times 10^5$ | $3.0 \times 10^5$ |
| | EDDS | $7.2 \times 10^4$ | ND | ND | ND | ND |
| C. pseudotropicalis | Dist water | $1.6 \times 10^5$ | $1.4 \times 10^6$ | $3.1 \times 10^6$ | $2.5 \times 10^6$ | $3.6 \times 10^6$ |
| | EDDS | $9.8 \times 10^4$ | $1.3 \times 10^3$ | ND | ND | ND |
| Fusarium sp. | Dist water | $4.4 \times 10^4$ | $5.8 \times 10^3$ | $1.4 \times 10^6$ | $9.6 \times 10^5$ | $3.0 \times 10^5$ |
| | EDDS | $1.4 \times 10^4$ | ND | ND | ND | ND |
| Penicillium sp. | Dist water | $98 \times 10^5$ | $1.3 \times 10^5$ | $4.0 \times 10^5$ | $2.5 \times 10^5$ | $2.4 \times 10^6$ |
| | EDDS | $6.3 \times 10^5$ | $1.2 \times 10^5$ | $9.5 \times 10^4$ | $8.9 \times 10^4$ | $7.4 \times 10^4$ |

ND = Not detected

All organisms used in the challenge test were able to survive in significant numbers in distilled waster, and some appeared to showed evidence of growth (see data in FIGS. 12 to 19). This confirmed the viability of the test organisms during the period of the study.

Fusarium and Penicillium were selected for the challenge test because of their partial resistance to EDDS displayed in the agar diffusion assays. Conversely Aeromonas and *C. pseudotropicalis* were included as control organisms because of their sensitivity to EDDS, as detected by agar diffusion assay.

Aeromonas and *C. pseudotropicalis* were also susceptible to EDDS in the challenge test, as neither organism was detected in significant numbers from Day 1 of the study.

Although Fusarium displayed low sensitivity to EDDS in the agar diffusion assay, it was very susceptible in the challenge test, as none of the original inoculum was detected on Day 1 or throughout the rest of the study.

There was a significant reduction in the concentration of Penicillium during the challenge test, although small numbers of this organism remained viable in EDDS throughout the 7 days of the study.

None of the rest organisms appeared capable of exponential growth in EDDS, notably including those that displayed some resistance to the inhibitory properties of EDDS by agar diffusion.

Modifications of the present invention will be apparent to those skilled in the art.

What is claimed is:

1. A method of preventing fungal growth on a material, the method comprising contacting the material with an amino acid derivative in free acid or salt form, in which the nitrogen atoms of two or more amino acid molecules are linked by a hydrocarbyl or substituted hydrocarbyl group, wherein the amino acids are naturally occurring amino acids; and wherein the amino acid derivative has at least one chiral centre.

2. A method of preventing fungal growth and bacterial growth on a material, the method comprising contacting the material with an amino acid derivative in free acid or salt form, in which the nitrogen atoms of two or more amino acid molecules are linked by a hydrocarbyl or substituted hydrocarbyl group, wherein the amino acids are naturally occurring amino acids; and wherein the amino acid derivative has at least one chiral centre.

3. A method of preventing bacterial growth on a material, the method comprising contacting the material with an amino acid derivative in free acid or salt form, in which the nitrogen atoms of two or more amino acid molecules are linked by a hydrocarbyl or substituted hydrocarbyl group, as an anti-bacterial compound, wherein the amino acids are naturally occurring amino acids; and wherein the amino acid derivative has at least one chiral centre with proviso that the amino acid derivative is other than a chelant selected from derivatives of succinic acid, glutaric acid and phosphonic acid.

4. The method of claim 3 for preventing fungal growth and bacterial growth.

5. The method of claim 1 wherein the amino acid derivative has at least two chiral centres.

6. The method of claim 5 wherein the amino acid derivative is ethylene diamine disuccinic acid (EDDS).

7. The method of claim 6 wherein the amino acid derivative has at least one (S) chiral centre.

8. The method of claim 7 wherein the amino acid derivative has at least two (S) chiral centres.

9. A method of preventing fungal growth and bacterial growth on a material, the method comprising contacting the material with an amino acid derivative in free acid or salt form, in which the nitrogen atoms of two or more amino acid molecules are linked by a hydrocarbyl or substituted hydrocarbyl group, and wherein the amino acids are naturally occurring amino acids.

10. The method of claim 8 wherein the amino acid derivative is ethylene diamine disuccinic acid.

11. A method of preventing fungal growth on a material, the method comprising contacting the material with a composition comprising an amino acid derivative in free acid or salt form, in which the nitrogen atoms of two or more amino acid molecules are linked by a hydrocarbyl or substituted hydrocarbyl group, wherein the amino acids are naturally occurring amino acids; and wherein the amino acid derivative has at least one chiral centre.

12. A method of preventing fungal growth and bacterial growth on a material, the method comprising contacting the material with a composition comprising an amino acid derivative in free acid or salt form, in which the nitrogen atoms of two or more amino acid molecules are linked by a hydrocarbyl or substituted hydrocarbyl group, wherein the amino acids are naturally occurring amino acids; and wherein the amino acid derivative has at least one chiral centre.

13. A method of preventing bacterial growth on a material, the method comprising contacting the material with a composition comprising an amino acid derivative in free acid or salt form, in which the nitrogen atoms of two or more amino acid molecules are linked by a hydrocarbyl or substituted hydrocarbyl group, as an anti-bacterial compound, wherein the amino acids are naturally occurring amino acids; and wherein the amino acid derivative has at least one chiral centre with proviso that the amino acid derivative is other than a chelant selected from derivatives of succinic acid, glutaric acid and phosphonic acid.

14. The method of claim 11 wherein the compound comprises less than 50% w/w of the composition.

15. The method of claim 14 wherein the compound comprises less than 40% w/w of the composition.

16. The method of claim 14 wherein the compound comprises less than 30% w/w of the composition.

17. The method of claim 14 wherein the compound comprises less than 10% w/w of the composition.

18. The method of claim 14 wherein the compound comprises less than 1% w/w of the composition.

19. The method of claim 14 wherein the compound comprises less than 0.05% w/w of the composition.

20. The method of claim 11 wherein the composition has a pH in the range 5 to 12.

21. The method of claim 20 wherein the composition has a pH in the range 8 to 10.

22. A method of increasing the activity of at least one anti-fungal compound, the method comprising contacting a composition comprising the at least one anti-fungal compound with an amino acid derivative in, free acid or salt form, in which the nitrogen atoms of two or more amino acid molecules are linked by a hydrocarbyl or substituted hydrocarbyl group, wherein the amino acids are naturally occurring amino acids; and wherein the amino acid derivative has at least one chiral centre.

* * * * *